United States Patent
Summer

(10) Patent No.: US 7,214,058 B2
(45) Date of Patent: May 8, 2007

(54) DENTAL MATRIX POSITIONED BY SLIDABLY ENGAGED MATRIX RETAINER

(75) Inventor: John D. Summer, Portland, OR (US)

(73) Assignee: Dental Innovations LLC, Portland, OR (US)

( * ) Notice: Subject to any disclaimer, the term of this patent is extended or adjusted under 35 U.S.C. 154(b) by 0 days.

(21) Appl. No.: 11/102,600

(22) Filed: Apr. 8, 2005

(65) Prior Publication Data

US 2005/0244787 A1 Nov. 3, 2005

Related U.S. Application Data

(60) Provisional application No. 60/560,937, filed on Apr. 9, 2004, provisional application No. 60/562,613, filed on Apr. 14, 2004.

(51) Int. Cl.
*A61C 5/04* (2006.01)
(52) U.S. Cl. ................................................ 433/39
(58) Field of Classification Search ............ 433/38–40, 433/149
See application file for complete search history.

(56) References Cited

U.S. PATENT DOCUMENTS

| 348,628 A | 9/1886 | Hewett |
| 388,620 A | 8/1888 | Booth |
| 427,338 A | 5/1890 | Marshall |
| 545,754 A * | 9/1895 | Wishart ...................... 433/148 |
| 638,973 A | 12/1899 | Mehlig |
| 804,099 A | 11/1905 | Chase |
| 1,133,379 A | 3/1915 | Hollingsworth |
| 1,265,581 A | 5/1918 | Zurbrigg |
| 1,669,231 A | 5/1928 | Curran |
| 1,794,213 A | 2/1931 | Spahn |
| 1,935,481 A * | 11/1933 | Nelson ........................ 433/39 |
| 2,288,011 A | 6/1942 | Mizzy |
| 2,538,486 A | 1/1951 | Tofflemire |
| 2,591,745 A | 4/1952 | Toffelmire |
| 2,607,117 A | 8/1952 | Baughan |
| 2,618,065 A * | 11/1952 | McAfee ...................... 433/157 |
| 2,771,677 A * | 11/1956 | Curry ........................ 433/39 |
| 2,790,238 A | 4/1957 | Trangmar |
| 2,835,628 A | 5/1958 | Saffir |

(Continued)

FOREIGN PATENT DOCUMENTS

WO WO 01/43656 A1 6/2001

OTHER PUBLICATIONS

*Sullivan-Schein Dental Catalogue*, pp. 313-314 prior art, (no publication date on these sheets).

(Continued)

*Primary Examiner*—Ralph A. Lewis
(74) *Attorney, Agent, or Firm*—Klarquist Sparkman LLP

(57) ABSTRACT

A device is disclosed for applying and holding a dental matrix strip against the side of a tooth which is to be filled. An embodiment of the device comprises a split ring that slidably receives a matrix. The split ring in this embodiment can have cushions on its ends sized to resist passage through matrix apertures following insertion of such cushions through these apertures when these components are slidably coupled together. This embodiment can also comprise respective matrix slots that receive portions of the split ring to at least partially conform the shape of the matrix to the shape of the split ring.

28 Claims, 5 Drawing Sheets

U.S. PATENT DOCUMENTS

| | | | |
|---|---|---|---|
| 2,918,724 A * | 12/1959 | Thurman | 433/158 |
| 3,074,169 A | 1/1963 | Freeman | |
| 3,082,531 A | 3/1963 | Jacobsen | |
| 3,145,472 A | 8/1964 | Tofflemire | |
| 3,305,928 A | 2/1967 | Tofflemire | |
| 3,421,222 A | 1/1969 | Newman | |
| 3,628,249 A | 12/1971 | Wurl | |
| 3,842,505 A | 10/1974 | Eames | |
| 4,004,345 A | 1/1977 | Ely | |
| 4,024,643 A | 5/1977 | Eisenberg | |
| 4,373,915 A | 2/1983 | Comstock | |
| 4,482,319 A * | 11/1984 | Patch | 433/39 |
| 4,523,909 A | 6/1985 | Lazarus | |
| 4,563,152 A | 1/1986 | McClure | |
| 4,608,021 A | 8/1986 | Barrett | |
| 4,704,087 A | 11/1987 | Dragan | |
| 4,718,849 A | 1/1988 | Von Weissenfluh et al. | |
| 4,718,852 A * | 1/1988 | Galler | 433/148 |
| 4,909,736 A | 3/1990 | Ritter | |
| 5,330,353 A | 7/1994 | Wavrin | |
| 5,342,194 A | 8/1994 | Feldman | |
| 5,380,198 A * | 1/1995 | Suhonen | 433/39 |
| 5,505,618 A | 4/1996 | Summer | |
| 5,586,883 A | 12/1996 | Nakisher et al. | |
| 5,607,302 A | 3/1997 | Garrison et al. | |
| 5,899,694 A | 5/1999 | Summer | |
| 5,951,801 A | 9/1999 | Weissenfluh et al. | |
| 6,007,334 A | 12/1999 | Suhonen | |
| 6,142,778 A | 11/2000 | Summer | |
| 6,206,697 B1 | 3/2001 | Hugo | |
| 6,234,793 B1 | 5/2001 | Brattesani et al. | |
| 6,336,810 B1 * | 1/2002 | Bertoletti | 433/39 |
| 6,350,122 B1 | 2/2002 | Meyer | |
| 6,425,760 B1 | 7/2002 | Summer et al. | |
| 6,482,005 B1 | 11/2002 | Summer et al. | |
| 6,509,540 B1 | 1/2003 | Summer et al. | |
| 6,736,639 B1 | 5/2004 | Summer | |
| 2003/0186186 A1 * | 10/2003 | Hahn | 433/39 |
| 2005/0089813 A1 * | 4/2005 | Slone | 433/39 |

OTHER PUBLICATIONS

*Dental Products*, "Matrix Bands" product description, Jul. 1998.
*Dental Products Report*, Light-Curing Matrix, Nov. 1999.

* cited by examiner

DENTAL MATRIX POSITIONED BY SLIDABLY ENGAGED MATRIX RETAINER

CROSS REFERENCE TO RELATED APPLICATIONS

This application claims the benefit of applicant's Provisional Application No. 60/560,937, filed Apr. 9, 2004, and the benefit of Provisional Application No. 60/562,613, filed Apr. 14, 2004, which are incorporated herein by reference in their entirety.

FIELD

The present disclosure relates to the field of dental devices and in particular, to tooth inserts for positioning between teeth and related methods.

BACKGROUND

Each tooth has two proximal sides, usually in contact with respective proximal sides of two adjacent teeth. Class 2 cavities affect one or both of the proximal sides of a tooth. Filling a class 2 cavity typically requires holding a matrix band or strip against the side of the tooth being filled during the filling process in order to contain the filling material, much like a form is used to contain concrete being poured. When silver amalgam was used as the filling material, its density and compactability separated the adjacent teeth far enough to compensate for the thickness of a strip of stainless steel positioned between the teeth that was uniformly of a thickness from 0.0012 inch to 0.002 inch. Therefore, simple monolithic strips of stainless steel were used. With the development of resinous filling materials, the simple relatively thick strips of metal matrix materials of uniform thickness became inadequate, because they tend to leave a gap between the teeth after the strips have been removed.

The initial response of the industry was to increase the separation force produced by a matrix retainer. Forceful matrix retainers were developed to simultaneously hold a sectional matrix between the proximal surfaces of adjacent teeth and to drive the adjacent teeth apart far enough to compensate for the thickness of the matrix. The matrix retainers in such cases are typically split rings that are forcibly opened with a locking type of pliers that is also used to place rubber dam clamps around teeth. Such pliers are commonly known as rubber dam clamp forceps. In one common approach, a partially opened split retention ring is placed between the teeth where the sectional matrix is located with the split ring abutting the matrix. The retention ring is then allowed to close forcibly against the sectional matrix and its adjacent tooth to press the matrix against the tooth being treated. The matrix retainers in common use are all powerful split rings of heavy gauge material (metal or plastic), because, when seated, they must provide enough force to separate the teeth far enough to compensate for the thickness of the sectional matrix, 0.0012 inch to 0.0020 inch. Split rings of this type are made of thick enough material to generate clamping forces of from five to twenty pounds when their ends are separated (spread apart) by a distance that is about equal to the width of a tooth. After the retention ring is removed, the intention is that the previously separated teeth (separated by the retainer) spring back far enough to re-establish a fully contiguous relationship at an area called the contact area.

One problem with these powerful retention rings is that they cannot be used with large fillings. That is, such known retention rings deliver large compressive forces at the sides of the matrix and these forces can indent the sectional matrix or deform it in a portion of the area of the tooth being filled. A second problem with these powerful retention rings is that they are not suitable for use with the selectively thinned matrix materials which are now available (e.g., such as described in U.S. Pat. No. 5,505,618, to Summer; U.S. Pat. No. 6,425,760, to Summer et al.; U.S. Pat. No. 6,509,540, to Summer et al.; and U.S. Pat. No. 6,736,639, to Summer, all of which are incorporated by reference herein), because the forceful compression at the sides of the matrix can deform the matrix.

Another problem with known sectional matrix products and retention rings arises from difficulties in using such products. That is, sectional matrix products are generally placed in a patient's mouth in one step. The powerful retention ring which holds the matrix in position is placed in a second step. It is difficult to hold the matrix in a correct position while the retention ring is being placed around it.

SUMMARY

There is therefore a need for an improved dental matrix and retention mechanism for holding the matrix in position together with related methods.

In accordance with one embodiment, a new type of lightweight retention ring is disclosed that desirably applies force holding the matrix against the tooth receiving the filling only at a location that is further gingival than the gingival margin of the cavity preparation.

Also in accordance with an embodiment, a matrix and a matrix retention ring is disclosed that can be easily engaged outside of the mouth and then placed in one easy step inside the patient's mouth against the side of the tooth being filled.

An embodiment of a device is disclosed for creating a form to contain and shape the filling material on the proximal walls of a class 2 resinous filling. In accordance with an embodiment, an apertured matrix strip and a resilient split ring are disclosed wherein the apertured matrix strip is slidably positioned on the ring. The matrix and ring are desirably coupled together and engaged outside of a patient's mouth so that both the apertured matrix strip and engaged resilient split ring can be easily carried together into the mouth and seated against the tooth receiving the filling. Then, after the filling is completed, both matrix strip and resilient split ring can be easily removed together. The resilient split ring and matrix strip can be generally symmetrical, so they can be used for teeth located in any area of the mouth.

The ends of a resilient split ring in accordance with an embodiment are desirably embedded in respective cushions, desirably of a soft compressible material such as open celled foam rubber. When the split ring is at rest (not being spread apart), these two ends are desirably abutting or substantially abutting so that, when the ring is closed and positioned between two teeth, the cushions in which the ends of the split ring are embedded meet or nearly meet at their ends and also press against the entire or substantially the entire gingival edge of the matrix strip. The ability of a highly conformable and compressible cushion material, such as open celled or low density foam rubber, to adapt to almost any type of surface assists the matrix strip to form a tight seal even when there is a concavity on the side of the tooth being filled. Confining the pressure from the retention ring to the gingival edge portion of the matrix also allows the portions of the matrix above the gingival edge to be pushed out by the filling material or a suitable instrument as far as needed to create a good contact with the adjacent tooth.

The resilient split ring and the matrix are desirably coupled together in a manner that allows enough rotation between the ring and matrix so that they can be used whether the teeth are short or long and typically no matter where in the mouth the teeth are located.

The matrix can be in the form of a strip and can have a thinned area positioned against the area of the tooth where the cavity is to be filled. The matrix desirably has first and second apertures spaced from the respective ends of the matrix and sized large enough for passage of the ends (including cushions if any on such ends) therethrough. Desirably, cushions on such ends are compressed to allow the insertion of each end of the retainer through an associated one of the apertures with the compressed material then expanding to a cross-sectional dimension that is greater than the cross-sectional dimension of the associated aperture. Thus, the cushions or compressible material on the retainer expands after passing through an associated aperture and resists passage backwardly through the associate aperture to assist in maintaining the matrix on the retainer. The matrix can also include one or more retainer engaging slots at each of the ends of the matrix.

The present invention is directed toward novel and non-obvious aspects of matrices, retainers and combinations thereof, as well as to related methods, alone and in various combinations and sub-combinations with one another. There is no requirement that any or all of the problems of the prior art be solved. The claims below define the invention.

DETAILED DESCRIPTION

Figure 1:
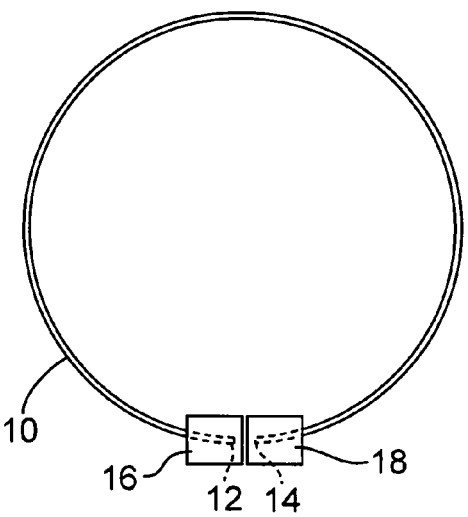
FIG. 1 shows a top view of one embodiment of a resilient split retention ring according to the present invention.
Figure 2:
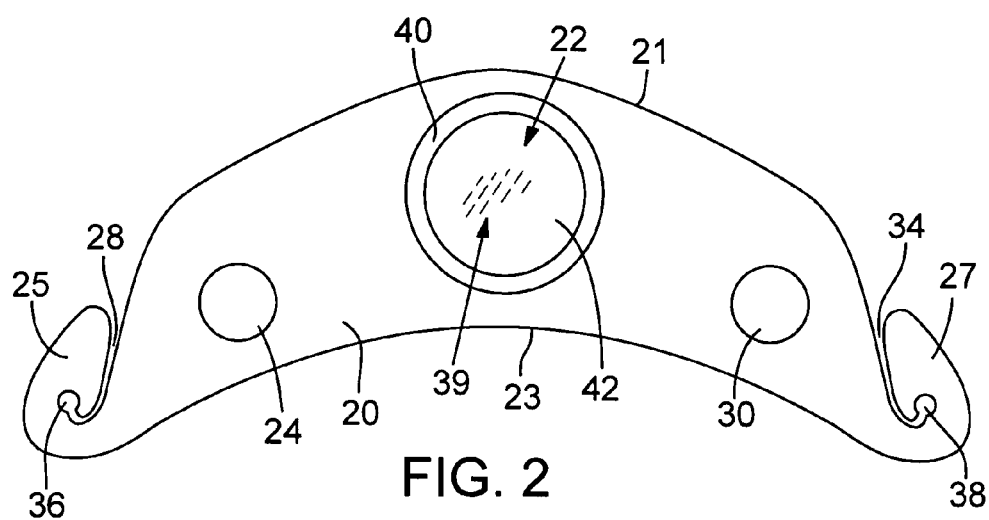
FIG. 2 shows a plan view of one embodiment of an apertured matrix.
Figure 2A:
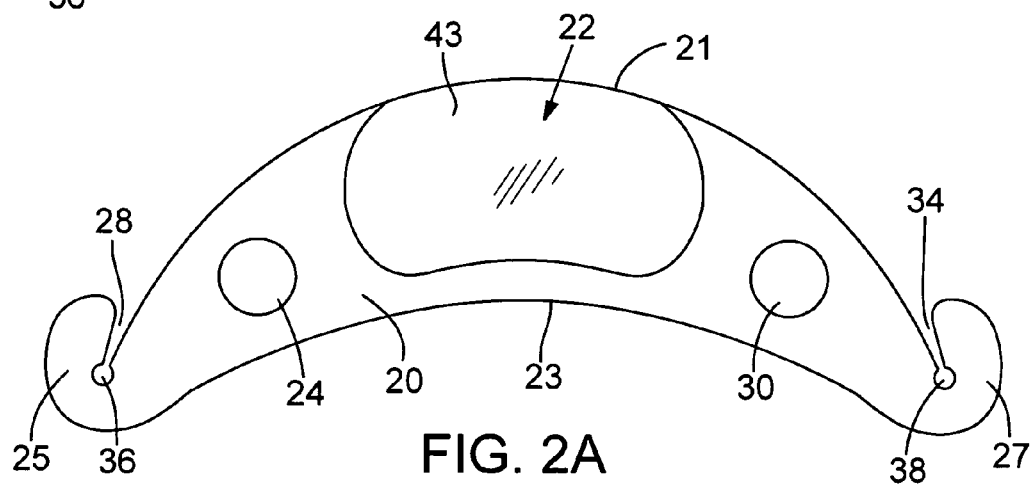
FIG. 2A shows a plan view of an alternative embodiment of an apertured matrix.
Figure 4:
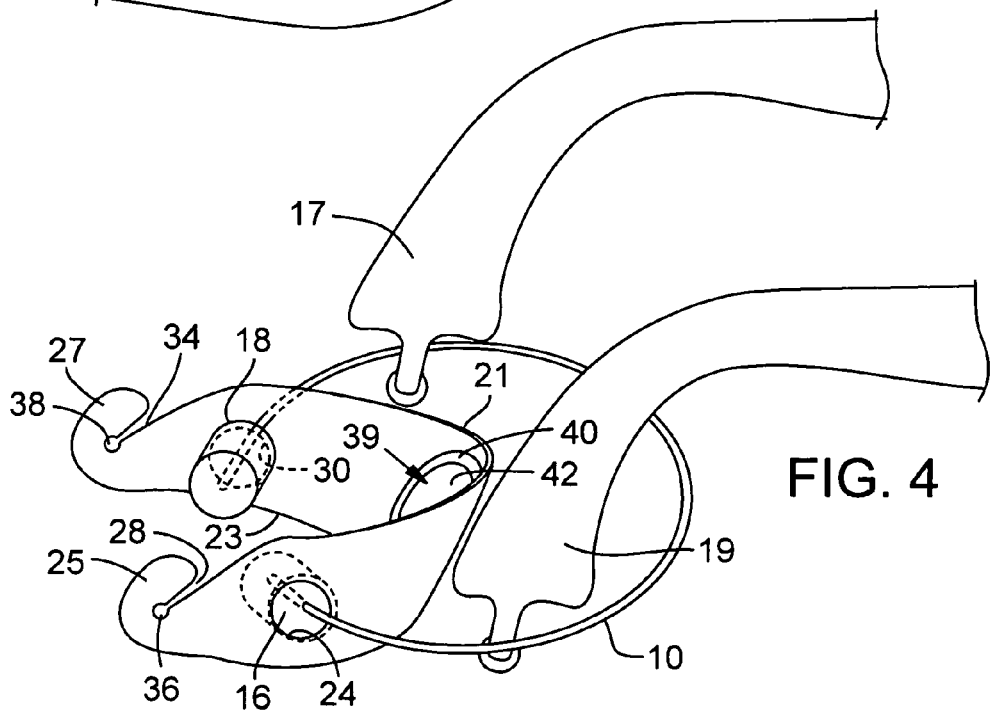
FIG. 4 shows a perspective view of a matrix with a window as in FIG. 2 and slots configured in the form shown in FIG. 2A and that has been bent to align two of the apertures therethrough, and with the retention ring of FIG. 3 being closed with respective cushions on the ends of the ring each being inserted through an associated matrix aperture.

An exemplary device for applying and retaining a matrix strip against the side of a tooth receiving a class 2 resinous filling desirably comprises two components, a lightweight resilient split retainer, such as a split retention ring illustrated in FIG. 1, and an apertured matrix, such as the matrix strip illustrated in FIG. 2, FIG. 2A, or FIG. 4. Other forms of such components may also be used.

FIG. 1 shows an embodiment of the resilient split retention ring 10 in its unstrained or resting state. The retention ring 10 in the disclosed embodiment is desirably lightweight and can, for example, be comprised of spring steel wire with a cross sectional diameter of, for example, from 0.02 to 0.03 inch with a specific desirable example being 0.025." Such a ring exerts minimal force against teeth as the ring is not required to wedge adjacent teeth apart. For example, such an exemplary ring exerts a closing force of from about five ounces to ten ounces when spread apart a distance about equal to the width of a tooth. A suitable retention ring can also be comprised of a number of different metals or plastics. The illustrated retention ring is shown in a generally circular shape, is generally planar, and has split end portions that terminate in close proximity to or abutting one another when the ring is relaxed. It is to be understood that the retention ring can also be oval, triangular, rectangular, or any other shape which is suitable for fitting around a tooth. Thus, the term ring is not limited to a circular shape and encompasses other shapes and desirably substantially closed geometric shapes. Also, a ring of wire having a circular cross-section assists in allowing the ring to slide relative to an engaged matrix (as explained below), but this is not required. The diameter of the circular shape of the disclosed retention ring 10 is about 0.4", making it large enough to fit around a large molar. Although variable, a ring that has a cross-sectional dimension that is longer than the longest tooth to which the ring is to be applied is most desirable, although the ring need not have the same cross-sectional dimension in all directions. A ring that has a diameter that is about 1.5 times the diameter of a large molar is particularly suitable. The illustrated retention ring 10 is continuous except for ends 12 and 14 bordering its split.

Affixed to the ends 12 and 14 of the retention ring 10 are cushions, such as of a right cylindrical shape and of an open celled foam rubber tips 16 and 18. Other materials may also be used for the cushions. Desirably, the selected material, whether it be rubber or a polymer for example, has a high degree of conformability so as to readily be inserted in the space at the gingival of the teeth and below the gingival boundary of the cavity to be filled and to readily assume the shape of adjoining tooth surfaces when the ring 10 is positioned (see e.g., FIGS. 9 and 10). In the described embodiment, open celled foam rubber tips 16 and 18 have the shape of right cylinders with their distal ends, for example, located one half millimeter beyond the ends 12 and 14 of the retention ring 10. Although variable, an exemplary diameter of such cushions is from 0.03 inch to 0.2 inch. As a result, the ends of the cushions are desirably fully contiguous or abutting when the retention ring 10 is at rest. Other cushion shapes may be used, such as cones that taper to an apex to mimic the natural anatomical shape of the interproximal (between the proximal surfaces of adjacent teeth) area. However, cushions having a right cylindrical cushion shape are desirable as such cushions provide a steady pressure against the matrix along substantially the entire gingival edge of the matrix in the region of the filling.

The foam rubber of cushions 16 and 18 is desirably open celled to give these cushion structures high compressibility. The compressibility of the foam enhances the adaptation of the gingival edge of the matrix against teeth with unusual shapes, such as when the gingival border of the proximal side of the tooth has a concavity.

The cushions 16 and 18 are desirably affixed to respective ring ends 12 and 14, such as by a heat welding process in the case of spring steel ring 10. One method of heat welding cushions 16 and 18 to ends 12 and 14 is by a process of: (a) forcing the ring 10 open to force ends 12 and 14 apart; (b) heating ends 12 and 14; (c) placing cushions 16 and 18 between hot ends 12 and 14; and (d) allowing ring 10 to close so the hot ends 12 and 14 are respectively each driven into the center of an associated cushion 16 or 18. Alternatively, the hot ends 12 and 14 can be allowed to close into each end of a single piece cylindrical cushion that is placed between such ends to thereby affix the ring ends to the cylinder. The cushion is subsequently cut in the middle and can be shaped, such as by a hot wire, to a more conical shape or other shape, if desired. It is understood that, other ways of performing heat welding of the cushions 16 and 18 to the ends 12 and 14 can also be used. In addition, friction, adhesives or cements may be used, rather than heat welding, to affix the compressible cushions to the ends of the resilient split ring.

FIGS. 2, 2A and FIG. 4 show exemplary forms of an apertured matrix that are designed so that they can be easily engaged by retention ring 10. With reference to FIG. 2, the illustrated matrix is in the form of a strip 20 comprising an elongated panel having a pair of opposite transversely spaced sides or ends 25 and 27, a gingival edge 23 and an occlusal edge 21. The term gingival edge refers to the edge of the matrix that is to be positioned closest to the gumline when the matrix is in use, and the term occlusal edge refers to the opposite edge, located farthest from the gumline and closest to the biting surfaces of the teeth.

Figure 8:
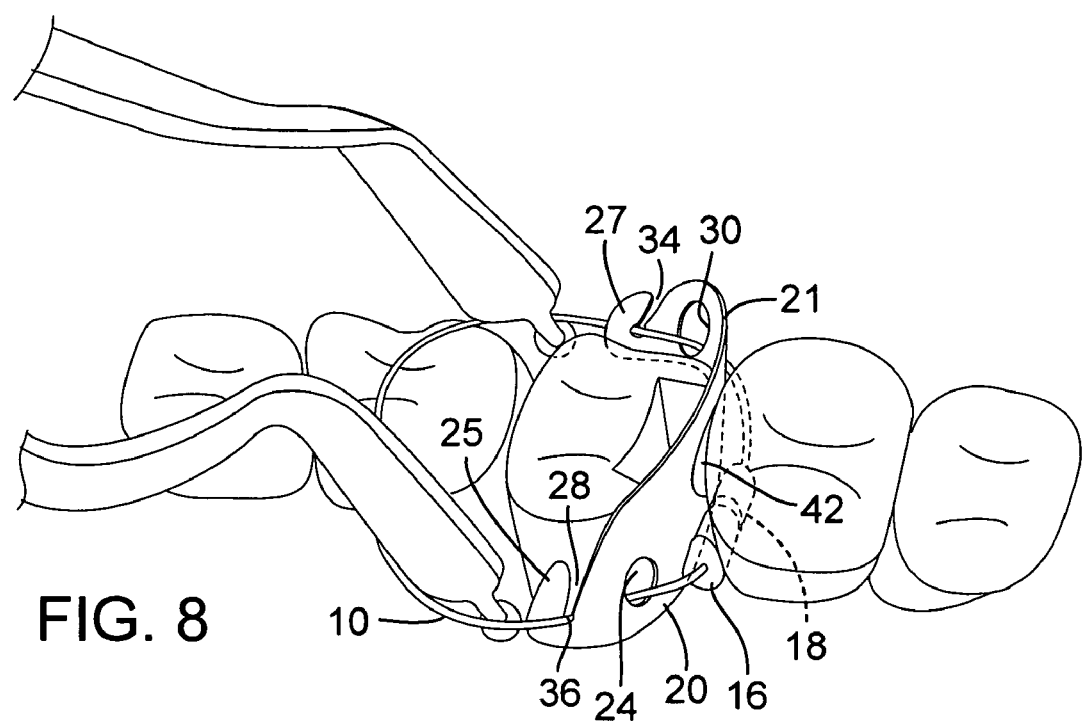
FIG. 8 shows a top perspective view of the engaged split ring and matrix strip of FIG. 7 after the ring is spread to allow positioning of the assembly in a patient's mouth with the matrix placed against the side of a tooth being filled
Figure 9:
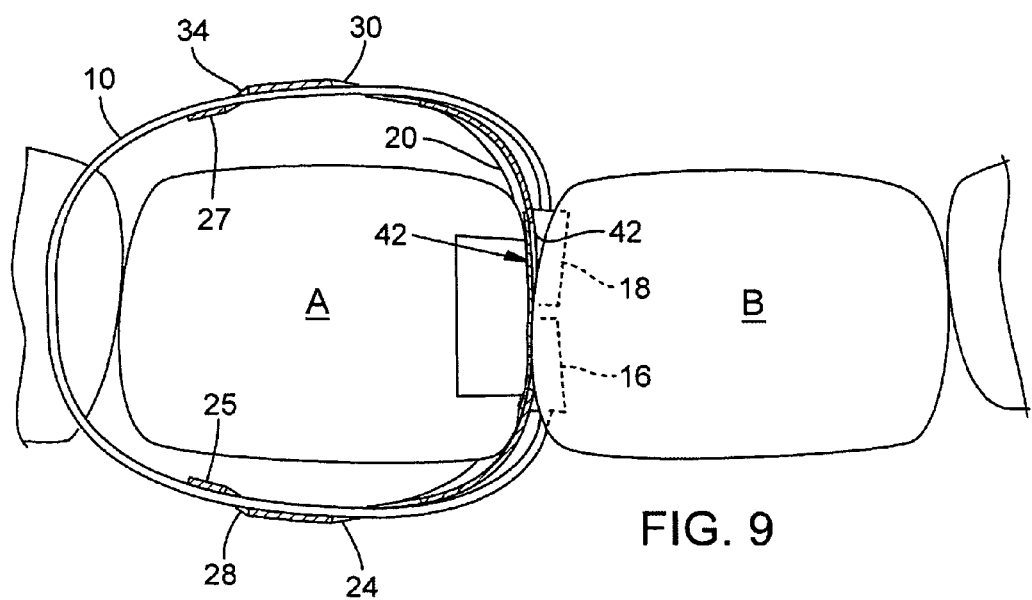
FIG. 9 shows a top view of the ring and matrix strip of FIG. 8 in position to allow the filling of a tooth.
Figure 10:
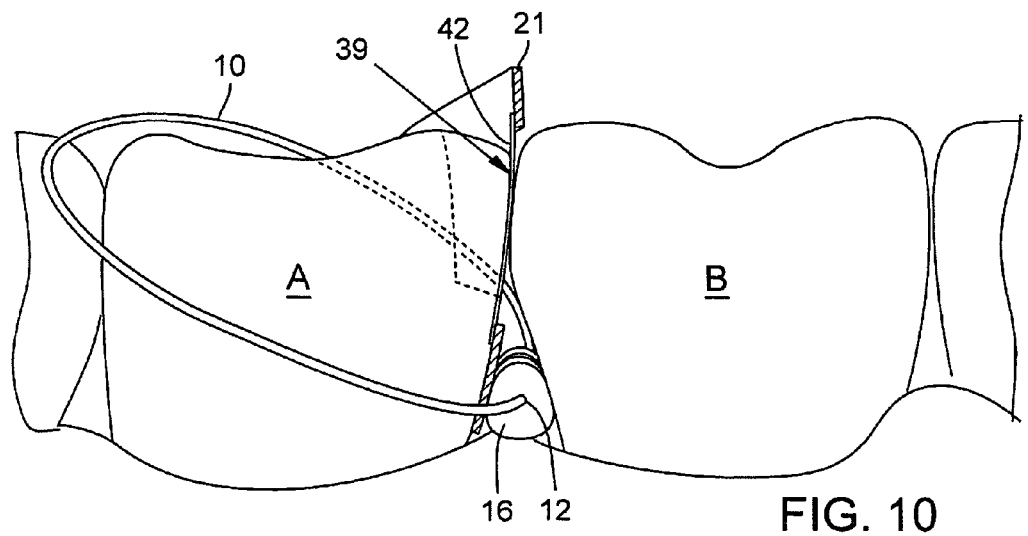
FIG. 10 is a side view of the matrix and ring structure of FIG. 9 with portions of the matrix shown in cross-section.

The illustrated form of matrix strip 20 is desirably a generally somewhat rectangular panel that desirably has arcuate gingival and occlusal edges. The concavity of the gingival edge 32 generally fits the convex shape of the interproximal gingiva. It is recognized that a wide variety of shapes are also suitable. At or near the center of matrix strip 20 is a central contact area 22. This central contact area 22 is positioned directly between the proximal surfaces of the adjacent teeth A and B as seen in FIGS. 8–10 when the matrix strip is in place.

In the embodiment of FIG. 2 (and also in the embodiment of FIG. 4), the central contact area 22 is relatively thin and is desirably thinner than the remaining portions of the matrix. These remaining portions of the matrix assist in reinforcing the central contact area. In the form shown, although other shapes can be used, the contact area 22 is a round window comprised of a thin (0.0005") plastic film 39 which is heat sealed (or otherwise mounted) to the surrounding stainless steel framework of the matrix strip panel body all along the peripheral border 40 of a round hole 42 in the matrix. The thin plastic film is preferably made of 0.0005 inch thick polyethylene, but a variety of other thin plastic or polymeric films can also be used. Although not required, the film may also be transparent to facilitate the passage of light through the film to cure light activated filling material. The thin plastic film may be affixed to the peripheral border 40 of the round hole 42 by, for example, a process in which the thin plastic film is stretched circumferentially by a mechanical expansion device such as a camera lens shutter. The stretched film is then positioned directly over the round hole 42, and then the peripheral border of the stretched film is heat welded or adhesively secured to the stainless steel all along the peripheral border 40 of hole 42. To minimize the chances of failure at the joint between the plastic film 39 and metal matrix strip 20, the side of the matrix strip to which the plastic is affixed is desirably positioned in a patient's mouth facing the prepared tooth A that is receiving the filling rather than facing the adjacent tooth B, such as can be seen in FIG. 10.

The illustrated matrix 20 also comprises spaced apart apertures 24,30 adjacent to respective end or side portions of the matrix. That is, aperture 24 is positioned between contact area 22 and end 25 of the matrix while aperture 30 is positioned between contact area 22 and end 27. Although the apertures may be other shapes, the illustrated apertures 24 and 30 are circular in configuration. This facilitates sliding of the matrix along the ring 10 when the matrix is mounted to the ring. Desirably, the apertures 24,30 are of greater cross-sectional diameter than the diameter of the ring to facilitate this sliding motion. Also, the apertures are positioned nearer the gingival edge 23 of the matrix than the occlusal edge 21, for example, the centers of the respective apertures 24,30 are desirably below the center of the contact area and most desirably below the lower portion of the contact area. This facilitates the positioning of a cushion 16,18 along the gingiva so as to bear against the gingival portion of the matrix beneath the area of the tooth being treated when the matrix and retainer are in position. See for example FIG. 5 and FIG. 10.

Figure 6:
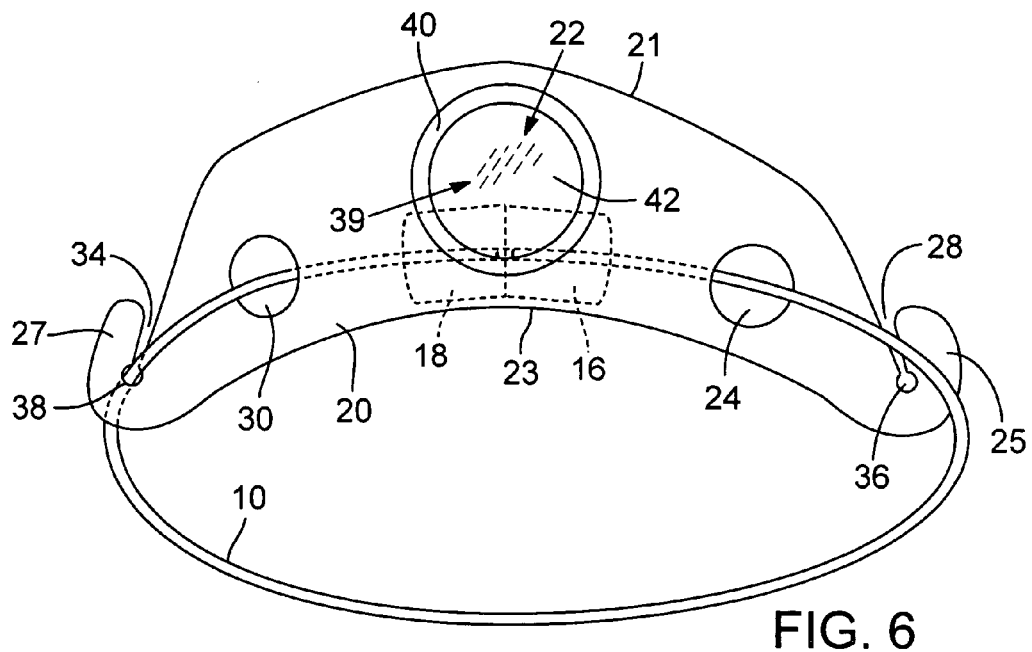
FIG. 6 shows a perspective view of the slidably carried resilient split retention ring and matrix strip of FIG. 5, and with one of the matrix end portions further engaged by the insertion of a portion of the ring into a slot located adjacent to the aperture of that matrix end portion.
Figure 7:
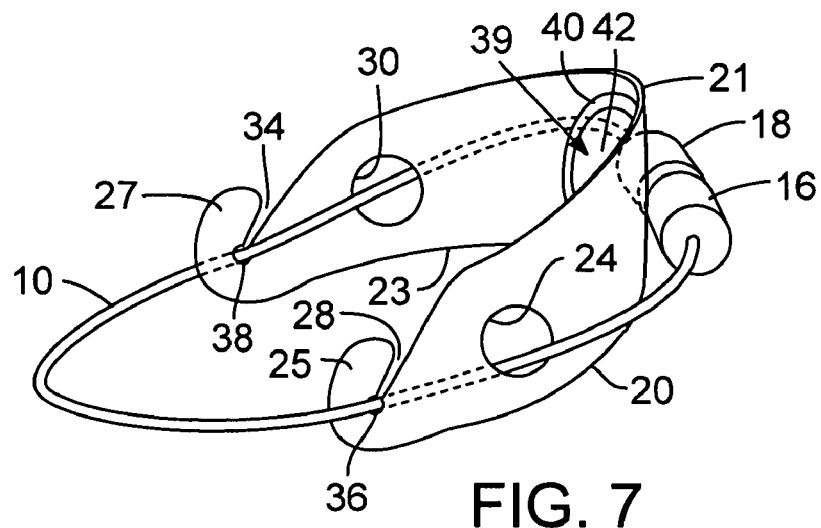
FIG. 7 shows a perspective view of the resilient split ring and matrix strip of FIG. 6 with another portion of the ring inserted into a slot at the other matrix end portion, and with the fully engaged matrix and ring ready to be placed against the side of a tooth being filled.

In addition, the illustrated matrix 20 shown in FIG. 2 desirably comprises respective spaced apart slots 28,34 positioned in respective buccal and lingual side portions adjacent the respective buccal and lingual sides or ends 25,27 of the matrix. These slots desirably extend from the occlusal edge of the matrix toward the gingival edge but terminate at a location spaced from the gingival edge 23. Also, each of the slots 28,34 in FIG. 2 desirably has a recurved configuration in that it turns at its base to have a section that extends toward the occlusal edge of the matrix. Thus for example, slot 28 together with its lowermost recurved portion may be generally of a J-shaped configuration with slot 34 being a mirror image of slot 28. Slot 28 terminates at its lower end in an enlarged retainer ring receiving slot hole or pocket 36 while slot 34 terminates in a similarly enlarged slot hole or pocket 38. As can be seen in FIGS. 6 and 7, portions of the retainer ring 10 may be inserted into the respective slots 28,34 and into position in the respective pockets 36,38. Desirably, the slot has a width that is greater than or equal to the diameter or cross-sectional dimension of the portion of the ring inserted into the slot so that the ring portion can easily pass through the slot and into the associated slot hole or pocket. The shape of the slot assists the matrix in capturing the portion of the ring and retaining the captured portion in either the respective pocket 36 or the respective pocket 38. When fully engaged, as shown in FIG. 7 (although FIG. 7 illustrates a matrix with slots of the FIG. 2A configuration), the assembly may be carried to a patient and inserted into a patient's mouth. Thus, the assembly may be completed outside of the confines of the patient's mouth prior to use. It should be noted that slots 28 and 34 are not required even though they are desirable. In addition, these slots may assume other configurations and other techniques may be used to engage portions of the retainer with the matrix. However, the configuration illustrated in FIG. 2 offers a mechanically efficient structure for engaging a matrix with a retention ring. It should also be noted that pockets 36 and 38 can be of an enlarged cross-sectional dimension in comparison to the dimensions shown in FIG. 2 to facilitate sliding of the matrix relative to the ring when the matrix is mounted to the ring and the slots are engaged.

FIG. 2A is similar to FIG. 2 with like components of FIG. 2A being assigned like numbers to those shown in FIG. 2. Hence, the like components will not be discussed further. In the embodiment of FIG. 2A, the contact area 22 is defined by a thinned region 43 of the matrix 20. That is, region 43 is of a lesser thickness than remaining portions of the matrix 20 such that the thinned region may readily be positioned between the teeth being repaired without spreading the teeth or interfering with adequate contact of adjoining teeth following the dental repair. Desirably, the thinned area is positioned to face the tooth that is not being filled so that a smooth matrix surface is positioned against the filled tooth, although this is not required. Also, the slots 28,34 of FIG. 2A are generally straight as opposed to recurved. In addition, these slots may narrow or neck down leading to the respective openings 36,38. The slots can, although not required, be of a width less than the diameter of the wire such as at the entrances to openings 36,38.

As a specific example, in one form shown in FIG. 2A, a tooth insert comprises an elongated band having at least one thin central region positioned so that, when the band is in position between two teeth, the thin central region is positioned between a first tooth and an adjacent second tooth. Thus, the thin central region is positioned between the interproximal surfaces of the first tooth and the second tooth at the proximal side of the first tooth, assuming that the first tooth is the tooth that is being treated. The body may include a reinforcing region extending partially or entirely around the thin central region. That is, the thin central region can, for example, extend entirely to the gingival edge of the body or may be spaced from the gingival edge by a reinforcing portion of the body. The central region may be enlarged in a direction toward the gingival edge of the body for use, for example, in cases where a deep filling is being completed. The thin interproximal contact areas or central regions typically range in thickness from about 0.0004 inch to somewhat less than 0.001 inch, with 0.0004 inch to 0.0007 inch being a preferred range and with a specific example being about 0.00045 to 0.0005 inch thick. The reinforcing region may vary in thickness with an exemplary range being from about 0.0015 inch to 0.003 inch. The superstructure or reinforcing portion of the insert or matrix maintains the overall rigidity of the insert and facilitates insertion of the insert in place against the side of a tooth that has been prepared for treatment, for example, for a class 2 filling.

The matrix bands of FIGS. 2, 2A and 4, at least the metal components thereof when made of stainless steel, may be manufactured using any convenient approach. For example, etching or other manufacturing approaches can be used, such as disclosed for example in the Summer and Summer et al. patents referenced in the Background section above, to form the apertures, slots and thinned areas of the FIG. 2A embodiment and also the window opening of FIG. 2. Using thinned contact areas reduces the need for wedging adjoining teeth apart to accommodate a matrix of full thickness. The matrices of FIGS. 2 and 2A have been shown with the thinned contact area (e.g., because of film 39 or thinned region 43). This is the most desirable construction. However, it is possible to provide a matrix without the thinned contact area but with structure such as apertures 24 and 30 and slots 28,34 to provide a matrix which may be engaged by a retainer for ready and convenient use in dental treatment activities. Also, although less desirable, a matrix structure having only one retainer ring receiving aperture and only one optional retainer receiving slot may be used.

Figure 3:
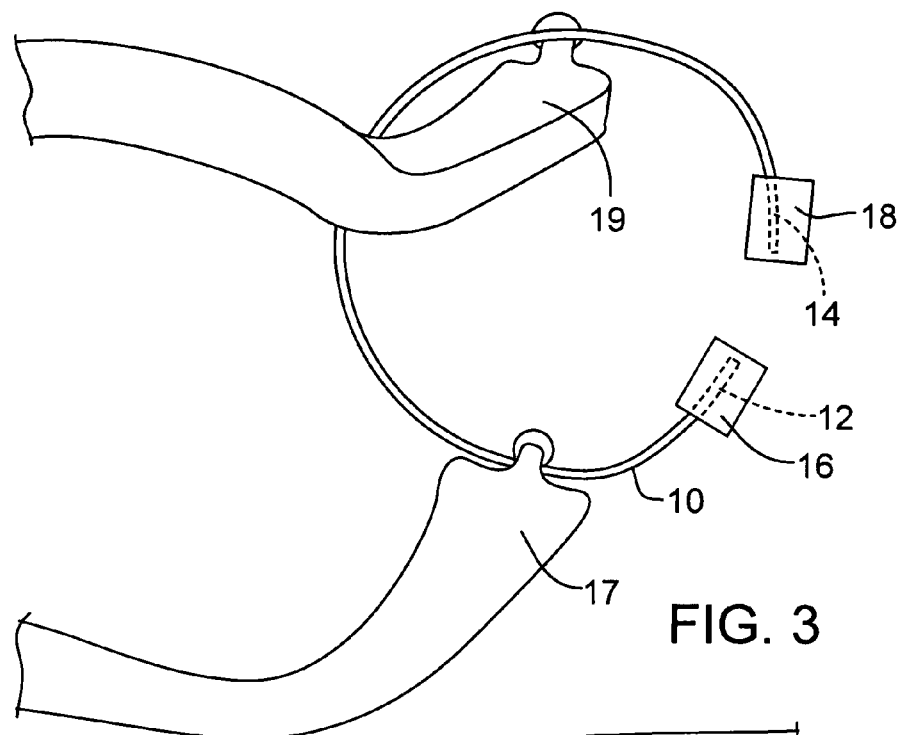
FIG. 3 shows a view of the resilient split retention ring of FIG. 1 in a position forced open by the tines of a retention ring spreader such as a rubber dam clamp forceps.

FIG. 4 shows how an exemplary resilient split ring is slidably engaged with the apertures of an exemplary apertured matrix strip. FIG. 3 shows the resilient split ring having been forced open by the jaws 17 and 19 of a locking pliers, such as a conventional rubber dam clamp forceps. FIG. 4 shows the position of the resilient split ring 10 and the compressible cushions 16,18 covering the respective ring end portions as the end portions and the cushions are passed through respective apertures 24 and 30 when the resilient split ring 10 is allowed to close back to its relaxed state. In this example, cushion 18 is shown being inserted through associated matrix aperture 30 and cushion 16 is shown being inserted through associated matrix aperture 24.

Figure 5:
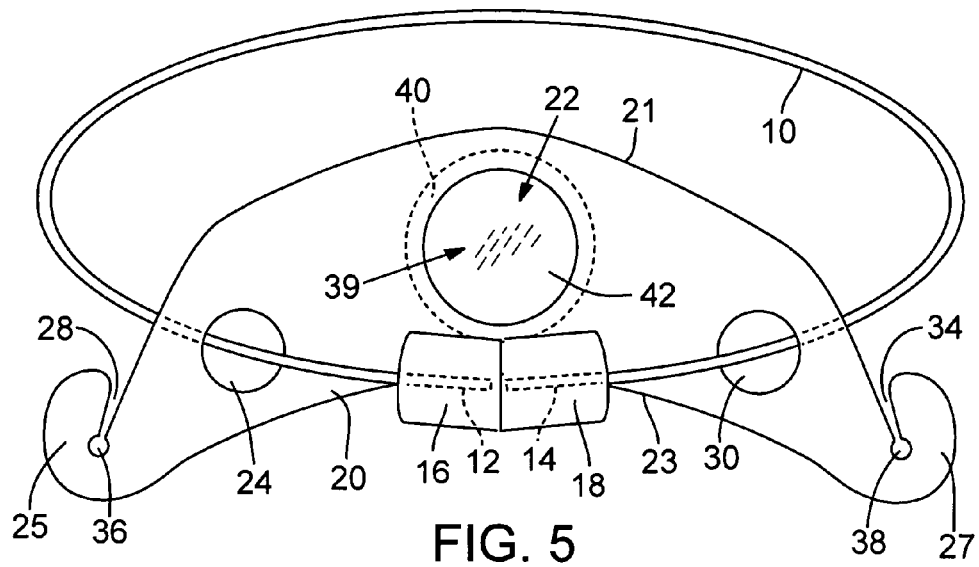
FIG. 5 shows a perspective view of the ring and matrix of FIG. 4 after the matrix is slidably positioned on the ring and after the cushions have been inserted through the respective matrix apertures.

FIG. 5 shows resilient split ring 10 and matrix strip 20 after having been slidably engaged by inserting the cushions through the apertures on each side of matrix strip 20.

FIG. 6 shows resilient split ring 10 and matrix strip 20 after having been slidably engaged by inserting the cushions through of the apertures on each side of matrix strip 20 and then with one end of the matrix having been further slidably engaged by means of seating a portion of the resilient split ring 10 through slot 28 and into an opening 38 at the termination of slot 28.

FIG. 7 is a perspective view showing the slidably engaged resilient split ring 10 and apertured matrix strip 20 after full engagement (a portion of split ring 10 also being positioned via slot 28 into opening 36) and ready to seat in a patient's mouth. The slots of the matrix of FIG. 7 are like those of the FIG. 2A matrix while the matrix of FIG. 7 has a central windowed region with a film like that shown in FIG. 2.

FIGS. 8–10 illustrate how cushions 16 and 18 are positioned with regard to matrix strip 20 after split ring 10 and slidably engaged matrix strip 20 have been placed against the side of tooth A that has been prepared for a class 2 filling.

While the present invention has been described in accordance with several embodiments, it is to be understood that substitutions and alterations may be made thereto without departing from the spirit and scope of the following claims. I claim all such modifications, which fall within the scope and spirit of the following claims.

I claim:

1. A dental matrix comprising:
    an elongated body comprising a gingival edge, an ocelusal edge, and first and second end portions, terminating in respective first and second ends;
    the body comprising a first central portion of a first thickness positioned between said first and second end portions and reinforcing portions adjacent to said central portion and of a second thickness that is greater than the first thickness;
    a first retainer receiving aperture positioned between the first central portion and the first end of the body, a second retainer receiving aperture positioned between the first central portion and the second end of the body; and
    a first retainer engaging slot at the first end portion of the body and nearer to the first end than the first aperture, the first retainer engaging slot terminating in a slot opening at the occlusal edge of the body, a second retainer engaging slot at the second end portion of the body and nearer to the second end than the second aperture, the second retainer engaging slot terminating in a first slot opening at the occiusal edge.

2. A dental matrix according to claim 1 in which the body comprises a band of uniform thickness except at the first central portion.

3. A dental matrix according to claim 2 in which the first central portion comprises a window in the body overlaid by a transparent plastic film.

4. A dental matrix according to claim 2 in which the band is a monolithic stainless steel band and the first central portion is a thinned region of the band having a reduced thickness between 0.0004 and 0.001 inch.

5. A dental matrix according to claim 1 in which each of the first and second retainer engaging slots has an enlarged retainer portion receiving opening spaced from the slot opening.

6. A dental matrix according to claim 1 in which one of the first and second retainer engaging slots is J-shaped and the other of the first and second retainer engaging slots is a mirror image of a J-shape.

7. A dental matrix according to claim 1 in which the first and second retainer receiving apertures each have a center that is positioned nearer to the gingival edge than to the occiusal edge.

8. A dental matrix according to claim 1 in combination with a split retention ring having first and second ring end portions, a first cushion carried by the first ring end portion and a second cushion carried by the second ring end portion, the first and second cushions being positioned adjacent to one another when the split ring is closed, the first ring end portion being inserted through the first retainer receiving aperture and the second end portion being inserted through the second retainer receiving aperture, and a portion of the split ring being inserted into the first retainer receiving slot and another portion of the split ring being inserted into the second retainer receiving slot.

9. A dental matrix apparatus and retainer for applying and retaining the dental matrix of the apparatus against the side of a tooth that is to receive a filling, said apparatus comprising:
   a split ring having a resilient substantially planar main body and two ends that are contiguous or in close proximity when the ring is at rest, a cushion of a soft compressionable material being coupled to at least one of said ends; and
   a matrix strip to which said split ring is slidably engaged, said matrix strip comprising an elongated panel having a central contact area of reduced thickness, respective opposite occlusal and gingival edges, and also having a first buccal side or end and a second lingual side or end located on opposite sides of the central contact area, the matrix strip comprising at least one retainer receiving aperture spaced from the contact area and slidably receiving the split ring.

10. The device according to claim 9 comprising first and second of said cushions and wherein the ends of the resilient split ring are each embedded in a respective one of the first and second cushions.

11. The device according to claim 9 wherein the matrix strip comprises at least first and second of said apertures spaced from the contact area, and wherein the cross-sectional dimension of at least a portion of the cushion is equal to or greater than a cross-sectional dimension of the first and second apertures.

12. The device according to claim 9 wherein the matrix strip comprises at least first and second of said apertures spaced from the contact area, the matrix strip also comprising first and second slots, the first slot being positioned between the first aperture and the first end, the second slot being positioned between the second aperture and the second end, the first and second slots each having a width that is larger than a cross sectional dimension of the body of the split ring.

13. The device according to claim 12 wherein each of the first and second slots terminate in an opening spaced from the occlusal edge and that has a cross-sectional dimension that is larger than the width of the associated slot.

14. The device according to claim 9 wherein the main body of the split ring is formed from metal wire and wherein the ends of the split ring are embedded in respective cushions of an open cell foam rubber that are heat welded to the respective ends of the retention ring.

15. A method for positioning and holding a central portion of a matrix strip against the portion of the proximal surface of a tooth which is being prepared for filling a cavity, the central portion of the matrix being held at least in part at a location that is nearer to the gingival than the gingival border of the cavity preparation, said method comprising:
   inserting a resilient split ring through apertures located adjacent to but spaced from the buccal and lingual ends of a matrix strip so that the retention ring and matrix strip are slidably engaged, said apertures being spaced from the central portion of the matrix; and
   inserting the central portion of the matrix strip between two teeth, and pressing the ends of the split ring against gingival portions of the central portion of the matrix strip between the teeth and at a location nearer to the gingival than the gingival border of the cavity preparation.

16. A method for positioning and holding a portion of a matrix strip against the portion of the proximal surface of a tooth which is being prepared for filling a cavity, the matrix being held at least in part at a location that is nearer to the gingival than the gingival border of the cavity preparation, said method comprising:
   inserting a resilient split ring through apertures located adjacent to but spaced from the buccal and lingual ends of a matrix strip so that the retention ring and matrix strip are slidably engaged;
   inserting the matrix strip between two teeth, with the ends of the split ring applying a holding force against gingival portions of the central portion of the matrix strip between the teeth and at a location nearer to the gingival than the gingival border of the cavity preparation; and
   the method also comprising inserting portions of the resilient split ring into respective slots in buccal and lingual end portions of the matrix strip such that the matrix strip bends until it acquires the same general shape as the ring.

17. The method of claim 15 in which the act of inserting the resilient split ring into the matrix strip apertures comprises bending the matrix strip substantially in half, forcibly opening the resilient split ring to split apart the ends of the split ring, placing the split apart ends of the resilient split ring opposite the matrix apertures, and then allowing the resilient split ring to close around the matrix strip so that the previously split apart ends of the split ring approach one another as they close and pass through the respective matrix apertures.

18. A method for slidably engaging a split retention ring with an apertured matrix strip, the method comprising the steps of bending the matrix strip to align respective first and second apertures adjacent to respective end portions of the matrix strip, forcibly opening the retention ring so that its split ends separate, placing the split ends of the retention ring in alignment with the aligned first and second apertures, allowing the retention ring to close around the matrix strip so that the previously split apart ends of the split ring approach one another as they close and pass through the aligned first and second apertures, and maintaining the end portions of the split ring slidable relative to the apertures without locking the end portions to the apertures during use of the matrix.

19. A method for slidably engaging a split retention ring with an apertured matrix strip, the method comprising the steps of bending the matrix strip to align respective first and second apertures adjacent to respective end portions of the matrix strip, forcibly opening the retention ring so that its split ends separate, placing the split ends of the retention ring in alignment with the aligned first and second apertures, allowing the retention ring to close around the matrix strip so that the previously split apart ends of the split ring approach one another as they close and pass through the aligned first and second apertures; and the method also comprising inserting portions of the retention ring into slots of the matrix strip that are positioned such that the matrix strip acquires the same general shape as the retention ring following insertion of the portions of the retention ring into the slots.

20. A matrix in combination with a split ring having first and second end portions, the matrix being apertured such that the matrix can be slidably engaged by the resilient split ring, said matrix strip comprising an arcuate generally rectangular panel comprising a central contact area and having respective opposite occlusal and gingival edges and having respective opposite buccal and lingual sides located on opposite sides of the central contact area and extending between occiusal and gingival edges, at least one buccal or lingual side containing at least one apertures, the split ring being slidably positioned in said at least one aperture and being slidable relative to said at least one aperture without gripping portions of the matrix panel bounding the at least one aperture.

21. The matrix strip of claim 20 comprising at least one slot positioned at the at least one of the buccal and lingual sides, the slot extending to and being accessible from the occiusal edge of the matrix panel, having a diameter which is greater than the cross-sectional diameter of at least a portion of the ring, the ring being positioned in said at least one slot.

22. The matrix strip of claim 20 in which the central contact area comprises a plastic film that is affixed to the borders of a central aperture provided through the matrix at the central contact area.

23. The matrix strip of claim 22 in which the plastic film is affixed to the borders of the central aperture while the plastic film is being held in a stretched state.

24. A matrix strip according to claim 20 comprising a respective cushion body of compressible material mounted to each end portion of the split ring.

25. A method of making an apparatus for securing a matrix strip against a portion of a tooth just beyond the gingival border of a cavity preparation, said method comprising:

spreading apart the ends of a resilient split ring with its ends embedded in respective compressible cushions;

sliding the resilient split ring onto the matrix strip by passing respective ends of the split ring through respective apertures adjacent to end portions of the matrix strip.

26. The method of claim 25 also comprising aligning the matrix strip with the resilient split ring by positioning respective portions of the resilient split ring in respective slots located adjacent to each end of the matrix strip.

27. A method of making a retention ring for securing a matrix strip against a portion of a tooth just beyond the gingival border of a cavity preparation, the method comprising;

forcibly opening a resilient metal split ring so that its two ends are separated further than at rest;

placing between the separated ends of the resilient split ring at least one cushion body of compressible material;

heating the separated ends of the resilient split ring; and allowing the hot ends of the resilient split ring to close into the cushion body so that the metal ends and the cushion body are heat welded together.

28. The method of claim 27 wherein the act of placing comprises placing between the separated ends of the resilient split ring at least one cushion body of open celled foam rubber.

* * * * *

UNITED STATES PATENT AND TRADEMARK OFFICE
CERTIFICATE OF CORRECTION

| | |
|---|---|
| PATENT NO. | : 7,214,058 B2 |
| APPLICATION NO. | : 11/102600 |
| DATED | : May 8, 2007 |
| INVENTOR(S) | : John D. Summer |

It is certified that error appears in the above-identified patent and that said Letters Patent is hereby corrected as shown below:

In the Specification:
In column 3, line 67, "filled" should read --filled.--

In the Claims:
Col. 9; line 65; In Claim 12, "The device according to claim 9" should read --The device according to claim 1--
In Claim 20, "occiusal" should read --occlusal--
In Claim 20, "apertures" should read --aperture--
In Claim 21, "occiusal" should read --occlusal--
In Claim 27, "comprising;" should read --comprising:--

Signed and Sealed this
Fourth Day of January, 2011

David J. Kappos
*Director of the United States Patent and Trademark Office*

UNITED STATES PATENT AND TRADEMARK OFFICE
CERTIFICATE OF CORRECTION

PATENT NO. : 7,214,058 B2
APPLICATION NO. : 11/102600
DATED : May 8, 2007
INVENTOR(S) : John D. Summer It is certified that error appears in the above-identified patent and that said Letters Patent is hereby corrected as shown below:

In the Specification:
In column 3, line 67, "filled" should read --filled.--

In the Claims:
Column 9; line 65; In Claim 12, "The device according to claim 9" should read --The device according to claim 1--
Column 11; line 35; In Claim 20, "occiusal" should read --occlusal--
Column 11; line 36; In Claim 20, "apertures" should read --aperture--
Column 11; line 44; In Claim 21, "occiusal" should read --occlusal--
Column 12; lines 30-31; In Claim 27, "comprising;" should read --comprising:--

This certificate supersedes the Certificate of Correction issued January 4, 2011.

Signed and Sealed this
First Day of February, 2011

David J. Kappos
*Director of the United States Patent and Trademark Office*